United States Patent [19]

Yamada et al.

[11] 4,379,755

[45] Apr. 12, 1983

[54] GELATINIZING AGENT COMPOSITION, AND GEL AND AQUEOUS EMULSION PREPARED THEREFROM

[75] Inventors: Mikio Yamada; Yujin Tabata, both of Tokyo, Japan

[73] Assignee: Nihon Surfactant Industry Co., Ltd., Tokyo, Japan

[21] Appl. No.: 202,653

[22] Filed: Oct. 31, 1980

Related U.S. Application Data

[63] Continuation-in-part of Ser. No. 63,748, Aug. 6, 1979, abandoned.

[30] Foreign Application Priority Data

Aug. 10, 1978 [JP] Japan ................................. 53-97705

[51] Int. Cl.³ ...................... B01F 17/34; B01F 17/39; B01J 13/00
[52] U.S. Cl. .................................. 252/312; 252/314; 252/316; 252/356; 252/DIG. 1; 424/172; 424/361; 426/602
[58] Field of Search ................. 252/316, 356, DIG. 1, 252/312

[56] References Cited

U.S. PATENT DOCUMENTS

| | | | |
|---|---|---|---|
| 2,114,490 | 4/1938 | Harris | 252/311 X |
| 2,285,422 | 6/1942 | Epstein et al. | 252/316 X |
| 2,893,990 | 7/1959 | Hass et al. | 536/119 |
| 2,951,015 | 8/1960 | Berger | 424/114 |
| 3,311,561 | 3/1967 | Anderson et al. | 252/77 X |
| 3,536,816 | 10/1970 | Kellner | 424/312 X |

OTHER PUBLICATIONS

"The Encyclopedia of Chemistry", Second Edition, Van Nostrand Reinhold Co., 1966, p. 263.
"DK-ESTER", brochure, cover page, pp. 1 to 13, Dai-Ichi Kogyo Seiyaku Co., Ltd.

*Primary Examiner*—Richard D. Lovering
*Attorney, Agent, or Firm*—Berman, Aisenberg & Platt

[57] ABSTRACT

Stable and homogeneous gel is obtained by forming a solution of a hydrophilic sucrose fatty-acid ester and a hydrophilic liquid polyhydric alcohol and incorporating oil into the resulting solution. Thus-prepared gel is useful either per se or for producing stable aqueous emulsions by admixing water therewith.

Stable and homogeneous gel is also obtained by forming a solution of hydrophilic sucrose fatty-acid ester, hydrophilic liquid polyhydric alcohol and lipophilic polyhydric alcohol fatty-acid ester and adding oil to the thus-obtained solution. Such gel likewise yields a stable aqueous emulsion when admixed with water.

Neither the noted homogenous gel nor the noted stable emulsion is produced from the specified constituents when admixed in a different order from that specified.

47 Claims, No Drawings

GELATINIZING AGENT COMPOSITION, AND GEL AND AQUEOUS EMULSION PREPARED THEREFROM

CROSS-REFERENCE TO RELATED APPLICATION

This application is a continuation-in-part of parent copending application Ser. No. 063,748 filed on Aug. 6, 1979, and now abandoned. The entire disclosure of the parent application is incorporated herein by reference subject to the preference of the disclosure in this application hereinafter.

BACKGROUND OF THE INVENTION

1. Field of the Invention

This invention relates to a new gel useful for cosmetics and foods. It yields an emulsion when mixed with water; this emulsion is useful for cosmetics, medicines and foods.

2. Description of the Prior Art

Diverse gelatinizing agents have been employed in cosmetic, medicine and food industries for forming gels, for controlling viscosity and for improving "feel". Various types of gels, including hydrophilic and lipophilic type gels, are known. Lipophilic gel is prepared by dispersing a lipophilic gelatinizing agent in an oil component; hydrophilic gel is prepared by hydrophilic gelatinizing agents.

Sucrose esters are known nonionic surfactants having a meritorious absence of toxicity (U.S. Pat. No. 2,893,990). The HLB (Hydrophilic Lipophilic Balance) values of sucrose esters range widely from a hydrophilic to a lipophilic region (HLB from about 3 to 18). Lipophilic sucrose esters are used mainly to obtain W/O emulsions. Lipophilic sucrose esters or dextrin higher fatty-acid esters provide safe and nontoxic gelatinizing agents; however, the resultant gels have various disadvantages, e.g. non-homogeneity, poor feel (they are sticky or oily) and lack of water washability. Polar materials which do not dissolve in oil and fat cannot be dissolved in such gels.

On the other hand, industrial use of hydrophilic sucrose esters has been limited by their poor dispersibility in oil and poor emulsifying power.

It is not impossible to prepare an O/W emulsion with hydrophilic sucrose esters provided a larger amount of the esters is used or the aid of an additional emulsifier is resorted to. For instance, from 5 to 30 percent of sucrose is used in U.S. Pat. No. 2,951,015, but from 5 to 40 percent soap is also required to prepare a penicillin emulsion. A further serious disadvantage of such gels is that water-free gels are not available and that a gel containing a large amount of oil is not available.

An oil-in-polyhydric alcohol gel (O/W gel hereinafter) or a reverse type gel (W/O gel hereinafter) are much desired particularly for cosmetics and various purposes.

OBJECTS OF THE INVENTION

It is an object of the present invention to provide a new gel which eliminates the noted disadvantages in the prior art.

Another object thereof is to provide a new gelatinizing agent which is suitable for forming a gel containing a large amount of oil, i.e. water-soluble substance.

A further object thereof is to provide means for obtaining water-free gels, as well as O/W and W/O gels, and to provide the corresponding resulting gels.

An additional object thereof is to provide substantially non-toxic gels having good storage and self stability.

A still further object thereof is to provide a gel having good emulsifiability or washability when used in cosmetics.

Other objects of the invention will become apparent from the following description.

SUMMARY OF THE INVENTION

After many efforts to attain the objects, the present inventors succeeded by finding that, in a composition of at least (1) hydrophilic sucrose fatty-acid ester, (2) hydrophilic liquid polyhydric alcohol and (3) oil, a gel is formed only by mixing all of these ingredients without the oil, and adding the oil to the thus-prepared mixture. Such gel is transparent or semi-transparent and has numerous good characteristics which enable it to satisfy the previously-noted objects; moreover, it is capable of including a large amount of oil and yielding a fine and stable emulsion on admixture with water.

DETAILED DESCRIPTION OF THE INVENTION

1. Preparation of the Gel

Neither hydrophilic sucrose fatty-acid ester nor hydrophilic liquid polyhydric alcohol is miscible with oil. However, these two ingredients are miscible with each other.

When an oil is added to and mixed with a homogeneous solution of these two ingredients, the oil is effectively dissolved in the solution of the two ingredients to form a homogeneous gel.

On the other hand, addition of the solution to the oil does not yield a gel, and mixing the sucrose fatty-acid ester, the polyhydric alcohol and the oil together also fails to produce a gel.

2. Hydrophilic Sucrose Fatty-Acid Ester

A hydrophilic sucrose fatty-acid ester is a first essential component for gelatinization of oil. In the present invention hydrophilic sucrose fatty-acid ester is that having an HLB value of at least 8. However, the sucrose fatty-acid ester has prefereably an HLB value of at least about 10, more advantageously at least 12 and most preferably at least 14. Such sucrose fatty-acid ester is a mono-, di- or tri-ester or an admixture thereof, a mono-ester or an admixture containing a major part of mono-ester being preferred, the remainder being usually a mixture of di-, tri- and poly-ester in which remainder diester is dominant in commercially available products. For instance, commercially available sucrose stearate/palmitate consisting of about 40% of mono-ester and the balance of a mixture composed of di-, tri- and poly-ester has an HLB value 8. A higher mono-ester percentage provides a higher HLB value.

The fatty-acid residue (which may be either saturated or unsaturated) of the sucrose fatty-acid ester has from 6 to 24, preferably from 12 to 18, carbon atoms. The sucrose fatty-acid ester is, e.g., a laurate, a myristate, a palmitate, a stearate, an oleate, a linoleate, a ricinolate, a caprylate, a caprate or the like, or any mixture thereof. The noted esters are commercially available.

The sucrose fatty-acid ester comprises from 5 to 98 percent, preferably from 8 to 80 percent, most preferably from 9 to 50 percent, of the composition for gelatinizing the oil (gelatinizing agent composition).

3. Hydrophilic Liquid Polyhydric Alcohol

A hydrophilic liquid polyhydric alcohol is a second essential component for gelatinizing the oil.

The polyhydric alcohol, which is liquid at 30° C. and atmospheric pressure, is, for example, ethylene glycol, propylene glycol, isobutylene glycol, 1,3-butylene glycol, polyethylene glycol having a molecular weight not exceeding 1500, polypropylene glycol having a molecular weight not exceeding 500, glycerin, diglycerin or a mixture of two or more of such ingredients. Glycerin, diglycerin and their mixtures are preferred; glycerin is particularly advantageously used for cosmetics. The hydrophilic liquid polyhydric alcohol may be a liquid solution containing a minor amount of other liquid polyhydric alcohol than those listed hereinabove dissolved therein.

4. Lipophilic Polyhydric Alcohol Fatty-Acid Ester

A surface-active lipophilic polyhydric alcohol fatty-acid ester is preferably used together with the previously-noted two components as an optional third component for gelatinizing agent composition.

Oil is added to a mixture of hydrophilic sucrose fatty-acid ester, hydrophilic liquid polyhydric alcohol and, optionally, this component, and mixed therewith to obtain a gel. The three-component mixtures to which oil is added are preferably prepared by mixing the sucrose fatty-acid ester with the polyhydric alcohol fatty-acid ester and then mixing the thus-prepared admixture with the polyhydric alcohol.

The polyhydric alcohol fatty-acid ester should have an HLB value of not more than 6, preferably from 4 to 6.

Suitable polyhydric alcohol fatty-acid esters include known surface-active polyhydric alcohol fatty-acid esters, such as a fatty-acid ester of, e.g., glycerin, pentaerythritol, sorbitol, mannitol, diglycerin, sorbitan or propylene glycol, or a mixture of two or more such fatty-acid esters are employed. Particularly, esters of sorbitan and glycerin are used for cosmetics.

The fatty-acid residue of such esters has from 6 to 30, preferably from 12 to 18, carbon atoms. For the fatty-acid residue, for example, these described in Example 11 for hydrophilic Sucrose Fatty-acid Ester are useful.

Such ester is mono-, di- and tri-ester or a mixture thereof. A mono-ester or a mixture containing a major part of polyhydric alcohol fatty-acid mono-ester is preferred.

The resultant total HLB value of the sucrose fatty-acid ester and the polyhydric alcohol fatty-acid ester is at least 8.

The gelatinizing agent composition optionally comprises from 0.1 to 65, preferably from 1 to 50 and most preferably from 1 to 20, percent by weight of polyhydric alcohol fatty-acid ester.

The mixture of the gelatinizing composition is prepared at room or an elevated temperature. A temperature of from 50° to 90° C. is suitable for quick preparation of a homogenous solution.

5. Oil

The oil is one which is a water-insoluble liquid useful for cosmetics, medicines or foods. It is one particular oil or a mixture of two or more oils; it is optionally a homogeneous solution containing fat which is normally in solid state.

Exemplary oils or fats are those of vegetable origin (such as cacao butter, castor oil, olive oil, corn oil, soy bean oil, tubaki oil, cottonseed oil, sesame oil, safflower oil, Japan wax and coconut oil), those of animal origin (such as squalane, mink oil, turtle oil, beeswax, spermaceti and lanolin and derivatives thereof), oil of mineral origin (such as liquid paraffin, polybutene, vaseline, paraffin wax, ceresin, microcrystalline wax and polyethylene powder), natural and synthetic type of fatty-acid alkyl esters (such as isopropylmyristate, isocetylmyristate and cetylisooctansate), higher fatty-acids (such as isostearic acid and lauric acid) and higher alcohols (such as isostearyl alcohol, oleyl alcohol, cetyl alcohol and stearyl alcohol). In addition to cosmetic use, mineral oils, such as kerosene, spindle oil and other liquid hydrocarbon, may be gelatinized.

Gels are prepared according to this invention with an oil content of from 47 to 97, perferably from 50 to 95, most preferably 50 to 90, percent by weight. Gels comprising such a high oil content have not been prepared in practice, and they have numerous and readily apparent uses.

The optimum oil amount in the gel depends upon the kind of oil, too. In gelatinizing procedure, oils which are solid at room temperature are liquefied by heating for gelatinization. Such oils may also be gelatinized after solution in a liquid oil.

A small amount of water or lower alcohol is optionally employed for viscosity control insofar as such as compatible with the contemplated end-use of the gel.

Other compounds are optionally added to a composition of the present invention for various purposes without departing from the spirit of the invention. For example, antibiotics, hormones, vitamins and other medicinal agents are incorporated in compositions formulated for medicinal use. Perfume, pigment, dye and various inorganic powders are incorporated for cosmetics; various foods, for food products; and other surfactants or solvents, for detergent use.

The advantages of the gel according to the present invention are summarized as follows:

(1) non-toxicity
(2) excellent capacity for a large amount of oil and/or fat in the gel
(3) capable of water-free gel formation
(4) good emulsifiability and washability (for use with cosmetics)
(5) capacity of containing polar compounds
(6) good gel stability.

Furthermore, gel of the present invention can be employed for O/W gel or W/O gel provided the total HLB value and partial HLB value are selected properly.

A gelatinizing agent composition of a relatively higher total HLB value than about 12 is preferably applied for an O/W gel, while that of a relatively lower total HLB value is applied for W/O gel provided that the total HLB value thereof is not less than 8.

The term oil or fat denotes every kind of oil and/or fat of vegetable, animal and mineral origin, natural and synthetic, ester type and hydrocarbon type.

Accordingly, gel of the present invention is useful particularly in cosmetic, medicine and food industries. However, it does not exclude further use in various related or different fields of industries.

It is an important advantage of the gel of the present invention that it yields a fine and stable emulsion (by merely mixing the gel with water) which is in either the W/O type or O/W type.

When the sucrose fatty-acid ester, the polyhydric alcohol, the oil and water are mixed at the same time, no fine stable emulsion is obtained; merely a two-phase composition or a coarse unstable emulsion is produced.

The O/W gel forms with ease a fine oil-in-water type emulsion if mixed with water. Accordingly, the sucrose fatty acid ester which cannot be used in the conventional emulsifying manner due to a poor emulsifying property can be advantageously utilized in the form of O/W gel of the present invention for producing stable emulsion of various kinds of oily, water-insoluble phase components.

On the other hand, the W/O gel will form an water-in-oil emulsion with an improved stability than those in the prior art.

In respect to even the fact that such a stable emulsion can easily be produced, the gel of the invention provides a significant advantage, i.e. not only in an ultimate use as a gel per se but as an intermediate product or article for producing the emulsion in a significant reduction of the mass and volume for storage, transportation, a simplified container and the like.

Furthermore, the gelatinizing agent composition is also useful as an intermediate product for producing a gel and/or finally an emulsion and has advantages similar to those of the gel.

The polyhydric alcohol is one which is liquid at room temperature because the liquid polyhydric alcohol imparts a necessary mixing or stirring property to the gelatinizing agent composition whereto the oil is under stirring admixed in the gelatinizing process resulting in a uniform fine dispersion of the oil in the gelatinizing composition. If crystalloidal polyhydric alcohol, e.g. sucrose, is used in place of the liquid polyhydric alcohol in the gelatinizing agent composition, a crystallization would occur during storage, resulting in a gel break. Accordingly, the polyhydric alcohol should be liquid at room temperature for obtaining a stable gel.

The gelatinizing composition of two ingredients, (a) hydrophilic sucrose fatty acid ester and (b) hydrophilic alcohol, and that of three ingredients (a), (b) and (c) lipophilic polyhydric fatty acid ester, are summarized in Table 1.

TABLE 1

| component | content (% by weight) | preferable content (% by weight) |
|---|---|---|
| a | 5–98 | 8–80 |
| b | 95–2 | 92–20 |
| a + b | 100 | 100 |
| a | 5–98 | 8–80 |
| b | 95–2 | 95–5 |
| c | 0.1–65 | 1–50 |
| a + b + c | 100 | 100 |

Accordingly, the present invention also provides a gel containing a relatively small amount of safe surfactant material and a large amount of oil.

The invention is further illustrated by the following examples. Percents are expressed by weight.

EXAMPLE 1

Sucrose fatty-acid ester having an HLB value 16 (1.7 g, DK Ester F-160 Daiichi Kogyo Seiyaku Co., 70% mono-ester the balance is a mixture of di-, tri- and poly- ester wherein diester is dominant; 70% stearate and the remainder being palmitate) and glycerin (43.3 g) were mixed with each other under stirring at 60° C. to obtain a homogeneous solution. Soybean oil was added little by little thereto under stirring. Viscosity was measured and listed in the following Table 2.

TABLE 2

| Soy Bean Oil | | Viscosity (c.p.) | |
|---|---|---|---|
| weight (g) | Content (%) | $\times 10^4$ at 25° C. | Appearance |
| 4 | 8.2 | 0.2 | cloudy liquid |
| 8 | 15 | 0.3 | opaque liquid |
| 20 | 31 | 0.6 | opaque viscous liquid |
| 40 | 47 | 1.7 | transparent gel-like mass |
| 45 | 50 | 2.4 | transparent gel |
| 50 | 53 | 3.2 | " |
| 55 | 55 | 3.9 | " |
| 60 | 57 | 5.5 | " |
| 405 | 90 | scaled up | " |
| 1455 | 97 | " | " |
| 2205 | 98 | — | separated |

As is evident from the results, an opaque liquid was obtained, and the viscosity of the liquid does not increase when less than 10 g (about 18%) of the soy bean oil was added. However, and moreover, the viscosity of the gel increased steeply and a transparent gel was obtained when more than 40 g (about 47%) of the soy bean oil was added. However, the oil content range below 30% is still liquid but no gel at all. Generally, a viscosity of exceeding 10,000 c.p. would be necessary for a mass to be identified as a gel. An upper limit of the soybean oil is 97% for the gel formation, a greater content of the oil does not form a gel.

Water was further added to the resultant gel. An addition of a small amount of water maintains the mixture in a gel-like form, and a further incorporation of water changes the mass to an emulsion. However, there is no definite boundary therebetween.

Then, the resultant gel was added to water and dispersed, and thereby an O/W type of emulsion was obtained. In such case, the gel comprising a higher content of oil gave the finer emulsion, while most of known gels with known gelatinizing agent can not include such a high content of oil.

A gel according to the present invention can include a high content of oil and can give a good emulsion by adding and dispersing the gel in water.

Now, when in the above experiment the sucrose fatty acid ester, glycerin and the oil were mixed with each other together at the same time, or the mixture of the sucrose fatty acid ester and glycerin was added to the oil and stirred, such gel was not formed, and an oil phase separated.

Now, the above experiment was repeated using squalane, olive oil or liquid paraffin instead of the soy bean oil, and thereby the same good result as above was given.

Now, the above experiment was repeated using propylene glycol, diglycerin, or polyethylene glycol (M.W. 400) instead of the glycerin, and the same good result as above was given.

EXAMPLE 2

A gel was prepared in the same manner as in Example 1, using sugar mono-laurate (HLB value 16, 5%), glycerin (15%) and silicone oil (80%). This gel is transparent and good in nontoxicity, and useful for several kinds of releasing and antifoaming agents.

It produces a good emulsion when added to and admixed with water. In the prior art there has been no gel of silicone oil capable of emulsification.

EXAMPLE 3

A gel was prepared in the same manner as in Example 1, using 5% sugar mono-stearate (HLB value 15), 20% propylene glycol and 75% sesame oil. This gel is transparent and useful as an ointment base for hormones, antibiotics and the like.

EXAMPLE 4

A gel was prepared in the same manner as in Example 1, using 10% sugar mono-stearate (HLB value 15), 20% polyethylene glycol (M.W. 400), 10% polyethylene glycol (M.W. 1500) and 60% corn oil; mixing was effected without heating. The resulting gel was semitransparent and useful as a soft capsule for an internal medicine and as an ointment base for an external medicine.

EXAMPLE 5

X% Sucrose mono-oleate (HLB 16), Y% Glycerine mono-oleate (HLB 6) and Z% Glycerine were mixed together and heated at 80° C. with stirring (to form a homogeneous mixture) and then cooled. To the mixture obtained (10 g) olive oil (100 g) was added and mixed at room temperature. The thus-obtained gel stability was observed. The results are shown in Table 3.

TABLE 3

| Gelatinizing agent composition components (%) | Test No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| X | 5 | 5 | 9 | 9 | 20 | 50 | 50 | 50 | 25 | 98 | 80 | 80 |
| Y | 0 | 1 | 0 | 1 | 10 | 5 | 15 | 25 | 65 | 0 | 1 | 15 |
| Z | 95 | 94 | 91 | 90 | 70 | 45 | 35 | 25 | 5 | 2 | 19 | 5 |
| stability | F | G | G | Ex | Ex | Ex | Ex | Ex | F | F | G | G |

Stability evaluation
F: Fairly good
G: Good
Ex: Excellent
NG: Not Good

EXAMPLE 6

Example 5 was repeated, using liquid paraffin (100 g) and each gelatinizing agent composition (10 g) having components described in Table 4. The stability of each prepared gel was evaluated.

TABLE 4

| Gelatinizing agent composition components (%) | No. | | | | | | |
|---|---|---|---|---|---|---|---|
| | 1 | 2 | 3 | 4 | 5 | 6 | 7 |
| Sucrose mono-oleate HLB 16 | 25 | 35 | 45 | 55 | 65 | 0 | 100 |
| Sorbitan mono-oleate HLB 4.3 | 5 | 5 | 10 | 0 | 0 | 25 | 0 |
| Diglycerin mono-oleate HLB 5.5 | 0 | 5 | 10 | 20 | 30 | 25 | 0 |
| PEG (M.W. 400) | 70 | 55 | 30 | 15 | 0 | 40 | 0 |
| POE (4) diglycerin | 0 | 0 | 5 | 10 | 5 | 10 | 0 |
| Stability | Ex | Ex | Ex | G | F | NG | NG |

Note:
Tests No. 6 and 7 are merely comparative tests.
POE: polyoxyethylene

EXAMPLE 7

Gels for cosmetics were prepared in the same manner as Example 5 (with the ingredients listed below) to determine a desirable proportion of polyhydric alcohol. The components of the gelatinizing agent composition and the results are shown in Table 5. A cleansing gel having excellent waterwashability was obtained.

| | |
|---|---|
| Liquid paraffin | 60 g |
| Squalane | 6 g |
| Beeswax | 4 g |
| Cetyl isooctanoate | 10 g |
| Gelatinizing agent | 20 g |

TABLE 5

| Gelatinizing agent composition components (%) | No. | | | | | | | |
|---|---|---|---|---|---|---|---|---|
| | 1 | 2 | 3 | 4 | 5 | 6 | 7 | 8 |
| Sucrose mono-oleate | 97 | 93 | 83 | 68 | 48 | 8 | 5 | 25 |
| Glycerin | 2 | 5 | 15 | 30 | 50 | 90 | 95 | 70 |
| Sorbitan mono-stearate | 1 | 2 | 2 | 2 | 2 | 2 | 0 | 5 |
| Stability | G | G | G | Ex | Ex | Ex | G | Ex |
| Washability | G | G | G | Ex | Ex | Ex | G | Ex |

EXAMPLE 8

110 g of isopropyl myristate gels were prepared with 10 g of the gelatinizing agent compositions, as shown in Table 6, in the same manner as described in Example 5. The results are shown in Table 6.

TABLE 6

| Gelatinizing agent composition components (%) | No. | | | | | | |
|---|---|---|---|---|---|---|---|
| | 1 | 2 | 3 | 4 | 5 | 6 | 7 |
| Sucrose mono-palmitate | 95 | 75 | 50 | 30 | 9 | 5 | 4 |
| Glycerin mono-oleate | 3 | 20 | 20 | 10 | 1 | 5 | 20 |
| Glycerin | 2 | 5 | 30 | 60 | 90 | 90 | 76 |
| Stability | G | G | Ex | Ex | Ex | G | NG |

EXAMPLE 9

Gels were prepared with 100 g of isopropyl myristate and 10 g of gelatinizing agent composition to investigate the effect of the resultant total HLB. The results are shown in Table 7.

TABLE 7

| Gelatinizing agent composition components (%) | No. | | | | | |
|---|---|---|---|---|---|---|
| | 1 | 2 | 3 | 4 | 5 | 6 |
| X. Sucrose mono-oleate (HLB 16) | 80 | 70 | 50 | 35 | 27 | 16 |
| Y. Glycerin mono-oleate (HLB 6) | 15 | 25 | 45 | 60 | 65 | 70 |
| Z. Propylene glycol | 5 | 5 | 5 | 5 | 8 | 14 |
| Total HLB | 13.7 | 12.7 | 10.7 | 9.2 | 8.2 | 7.4 |
| Stability | Ex | Ex | Ex | G | F | NG |

The above experiment was repeated using liquid paraffin or olive oil instead of isopropyl myristate, sucrose mono-oleate (HLB value 16) for X, sorbitan mono-oleate for Y, or glycerin for Z. When a resultant total HLB balance of X and Y is not less than 10, any one of thus obtained gels was excellently stable and transparent.

EXAMPLE 10

Gels for lip cream were prepared with 10 g of beeswax, 10 g of Carnauba wax, 20 g of polybutene, 10 g of isopropyl myristate, 30 g of castor oil, 10 g of liquid paraffin and 10 g of gelatinizing agent composition. The gelatinizing agent compositions were composed of 40% sucrose fatty-acid ester, whose fatty acids have 12 to 18 carbon atoms, 20% glycerin mono-stearate and 40% diethylene glycol. Sucrose fatty-acid esters of laurate, myristate, palmitate, stearate and oleate were examined. All the gels using sucrose fatty acid ester with a major part (40–90%) of mono-ester showed good stability, and particularly 90–100% of mono-ester showed good feel.

EXAMPLE 11

Gels were prepared with the base oil composition same as Example 10 and gelatinizing agent composition comprising 40% sucrose mono-oleate, 20% polyhydric alcohol fatty acid esters of different fatty acid residues, 40% diglycerin. The tested combination of polyhydric alcohols and fatty acid residues of polyhydric alcohol fatty acid esters are illustrated in Table 8 by marking in "+".

TABLE 8

| Fatty acid residues | Polyhydric alcohols | | | | | | | | | | | |
|---|---|---|---|---|---|---|---|---|---|---|---|---|
|  | 1 | 2 | 3 | 4 | 5 | 6 | 7 | 8 | 9 | 10 | 11 | 12 |
| caproic |  |  |  | + |  |  |  |  |  |  |  |  |
| caprylic |  |  |  | + |  |  |  |  |  |  |  |  |
| lauric | + | + | + | + |  | + |  |  | + |  |  |  |
| myristic |  |  |  | + | + |  |  | + |  |  |  |  |
| palmitic |  |  |  | + | + | + | + | + |  | + |  |  |
| stearic | + | + | + | + | + | + |  | + | + | + | + | + |
| behenic |  |  |  | + |  |  |  |  |  |  |  |  |
| lignoceric |  |  |  | + |  |  |  |  |  |  |  |  |
| melissic |  |  |  | + |  |  |  |  |  |  |  |  |
| oleic | + | + | + | + | + | + | + | + | + | + | + | + |
| linoleic |  |  |  | + | + |  |  |  |  |  |  |  |
| linolenic |  |  |  | + |  |  |  |  |  |  |  |  |
| sorbic |  |  |  | + |  |  |  |  |  |  |  |  |
| lanolin fatty acid |  |  |  | + | + |  |  |  |  |  |  |  |
| isostearic |  |  |  | + |  |  |  |  |  |  |  |  |
| tall oil |  |  |  | + |  |  |  |  |  |  |  |  |

Polyhydric alcohols: 1. ethylene glycol, 2. diethylene glycol, 3. polypropylene glycol (M.W. 500), 4. glycerin mono-ester, 5. glycerin di-ester, 6. butyl alcohol, 7. pentaerythritol, 8. sorbitol mono-ester, 9. sorbitol di-ester, 10. mannitol, 11. glucose, 12. sucrose All the gels proved excellent stability and good feel.

EXAMPLE 12

Gels were prepared with the base composition (same as Example 10) and gelatinizing agent composition comprising 40 percent sucrose mono-oleate, 20 percent glycerin mono-stearate and 40 percent polyhydric alcohol. A different polyhydric alcohol was used in each gelatinizing agent composition. Examined polyhydric alcohols were ethylene glycol, dipropylene glycol, glycerin and hexanetriol. All of the resulting gels possessed excellent stability.

EXAMPLE 13

A cleasing gel having good water washability was prepared as follows.

| A mixture comprising: | | | |
|---|---|---|---|
| sucrose fatty-acid ester (mixture of 70% stearate and 30% palmitate; 70% mono-ester, the balance being a mixture of di-, tri- and polyester) | HLB 16 | | 30% |
| sorbitan mono-stearate | HLB 4.7 | | 10% |
| glycerin | | | 60% | was heated to 80° C. with stirring to a homogeneous mixture and then cooled. An oil (80%) consisting of liquid paraffin, squalane, beeswax and cetylisooctanoate (Weight Ratio-30:3:2:5) was added little by little thereto (20%). A semitransparent cleansing gel was obtained, which gel was stable after a long time. This cream was applied to hand or face and was then easily washed off with water.

EXAMPLE 14

A gel-like semitransparent suntan oil was prepared from the following constituents in the same manner as in Example 13.

| Gelatinizing agent composition | | | 12% |
|---|---|---|---|
| sucrose fatty-acid ester* | HLB 11 | 50% | |
| diglycerin mono-oleate | HLB 5.5 | 5% | |
| diglycerin | | 45% | |
| Olive oil | | | 88% |

*(DK ESTER F110 50% mono-ester; 70% stearate and 30% palmitate)

EXAMPLE 15

Gel-like bath oil was prepared from the following materials in the same manner as in Example 9.

| Gelatinizing agent composition | | | 30% |
|---|---|---|---|
| sucrose fatty-acid ester** | HLB 14 | 25% | |
| sorbitan mono-oleate | HLB 4.3 | 5% | |
| polyethylene glycol (M.W. 400) | | 70% | |
| Liquid paraffin | | | 70% |

**(DK ESTER F-140 40% mono-ester, the balance being a mixture of di-, tri- and polyester; 70% stearate and the balance palmitate)

It was a semitransparent gel which was easily emulsified in hot water. But, when all such ingredients were mixed with each other together at the same time, an emulsion was not obtained.

EXAMPLE 16

An ointment base was prepared from the following materials in the same manner as in Example 13.

| Gelatinizing agent composition | | | 40% |
|---|---|---|---|
| sucrose fatty-acid ester (same as in Example 13.) | HLB 16 | 15% | |
| sorbitan monostearate | HLB 4.7 | 3% | |
| polyethylene glycol (M.W. 300) | | 32% | |
| propylene glycol | | 50% | |
| Liquid paraffin | | | 30% |
| Isopropyl myristate | | | 20% |
| Cetanol | | | 10% |

The obtained gel was water washable, not sticky, and suitable for dissolving topically-applied medicinal agents; it was useful as an ointment base.

EXAMPLE 17

A W/O vegetable oil gel was prepared from the following materials in the same manner as in Example 13.

| Olive oil | 100g |
|---|---|

-continued

| Gelatinizing agent composition: | | 10g |
|---|---|---|
| sucrose laurate | HLB 17 | 40% |
| diglycerin mono-oleate | HLB 5 | 40% |
| glycerin | | 20% |
| (total HLB 11) | | |

Thus-prepared gel was a transparent jelly-like gel.

EXAMPLE 18

A homogeneous mixture of 1.0% sucrose monostearate (HLB value 15), 0.3% sorbitan monostearate (HLB value 4) and 0.2% glycerin monostearate (HLB value 5) was prepared. 10.0% glycerin was added thereto and stirred to give a homogeneous solution. To the solution 88.5% corn oil was added little by little and stirred to form an edible gel.

A fine emulsion was produced by adding this edible gel to water. The emulsion is useful as several kinds of food or food additive, such as synthetic milk.

EXAMPLE 19

A gel was prepared from the following materials in the same manner as in Example 18.

| Sucrose fatty-acid ester (HLB value 16) | |
|---|---|
| (palmitate 40%, stearate 60%, | |
| Mono-ester 70%, di-ester 30%) | 2.25 to 3.13g |
| Sorbitan monostearate (HLB value 4.7) | 1.87 to 2.25g |
| Glycerin | 5g |
| Liquid paraffin (viscosity 70 c.p. at 25° C.) | 50g |

No gel resulted from mixing these four ingredients together at the same time.

A gel prepared according to this Example was added to water (40 g) to give a fine emulsion, which was stable for a long time. Such emulsion is useful as a cosmetic or cosmetic base.

No emulsion resulted from mixing the noted four ingredients together with water at the same time; an oil phase separated out.

REFERENCE TEST 1

A. A semitransparent solution was prepared by adding corn oil (5 g) little by little under stirring to a homogeneous mixture of sucrose fatty acid ester (HLB value 16, "DK ESTER F-160" same as in Example 1, 1.7 g) and glycerin (43.3 g). A fine emulsion was prepared by adding such solution to water (50 g).

B. A cloudy solution was obtained by adding the corn oil and the sucrose fatty acid ester little by little under stirring to the glycerin. Thus obtained mixture was added to the water, and, however, thereby resulting in only an unstable coarse emulsion. Even apart from the range for gelatination of the present invention, it has turned out that the gelatinizing agent composition of the invention provides a good emulsifying property in comparison to the case the separate components are simultaneously mixed.

REFERENCE TEST 2

The same preparing manner as the second one in the Reference Test 1 was repeated except for using sorbitan mono-oleate (1.7 g) instead of the sucrose fatty acid ester. Neither a gel nor an emulsion was prepared. The resultant mixture separated into two phases.

As is evident from these results, it is understood that such hydrophilic sucrose fatty acid ester is essential for gelatinization and emulsifying of the oil, as well as the manner for mixing such ingredients.

REFERENCE TEST 3

A cloudy liquid of a medium viscosity (about 4000 c.p. at 25° C.), but not a gel at all, was obtained by admixing corn oil (5 g) little by little under stirring to the (homogeneous) mixture of the same sorbitan mono-oleate (1.7 g) same as one used in the Reference Test 2, sugar (8.66 g) and glycerin (34.64 g).

The invention and its advantages are readily understood from the preceding description. Various changes may naturally be made in the gelatinizing agent composition, and method of gel formation, the gel composition, the process of forming aqueous emulsions and the emulsion compositions without departing from the spirit or scope of the invention or sacrificing its material advantages. The processes, compositions and products hereinbefore described are merely illustrative of preferred embodiments of the invention.

What is claimed is:

1. An oil-free gelatinizing agent composition for gelatinizing oil and comprising from 5 to 98 percent by weight of (a) hydrophilic sucrose fatty-acid ester and from 95 to 2 percent by weight of (b) hydrophilic liquid polyhydric alcohol.

2. A gelatinizing agent composition according to claim 1 consisting essentially of (a) and (b).

3. A gelatinizing agent composition according to claim 1 in solution form and further comprising from 0.1 to 65 percent by weight based on the resultant composition of (c) surface active lipophilic polyhydric alcohol fatty-acid ester.

4. A gelatinizing agent composition according to claim 3 consisting essentially of (a), (b) and (c).

5. A composition according to claim 1 for gelatinizing oil which is a substantially or entirely water-free solution and comprises:
(a) hydrophilic sucrose fatty-acid ester,
(b) hydrophilic liquid polyhydric alcohol and, optionally,
(c) surface active lipophilic polyhydric alcohol fatty-acid ester,
the solution having, per 100 parts by weight, from 5 to 98 parts by weight of (a) and from 95 to 2 parts by weight, respectively, of (b); the amount of (c), when present, being from 0.1 to 65 percent by weight based on the total weight of (a), (b) and (c).

6. An entirely water-free solution according to claim 5.

7. A process for forming a homogeneous and stable gel composition which comprises adding oil to and admixing it with a composition according to claim 1 or claim 3.

8. A substantially water-free and homogeneous gel composition comprising oil incorporated in a gelatinizing composition according to claim 1.

9. A substantially water-free and homogeneous gel composition comprising oil incorporated in a composition according to claim 3.

10. A composition as set forth in claim 1, 8 or 9 wherein the sucrose fatty-acid ester has an HLB value of at least 8.

11. A composition as set forth in claim 1, 8 or 9 wherein the sucrose fatty-acid ester has an HLB value of at least 10.

12. A composition as set forth in claim 1, 8 or 9 wherein the sucrose fatty-acid ester has an HLB value of at least 12.

13. A composition as set forth in claim 1, 8 or 9 wherein the sucrose fatty-acid ester is at least about 40% by weight of sucrose fatty-acid mono-ester.

14. A composition as set forth in claim 13 wherein each sucrose fatty-acid mono-ester has a fatty-acid residue with a carbon content of from 6 to 24 carbon atoms.

15. A composition as set forth in claim 13 wherein each sucrose fatty-acid mono-ester has a fatty-acid residue with a carbon content of from 12 to 18 carbon atoms.

16. A composition as set forth in claim 13 wherein each sucrose fatty-acid mono-ester has a fatty-acid residue selected from the group consisting of that of lauric acid, that of myristic acid, that of palmitic acid, that of stearic acid and that of oleic acid.

17. A composition according to claim 11 wherein the sucrose fatty-acid ester consists mainly or entirely of sucrose fatty-acid mono-ester.

18. A composition as set forth in claim 1, 8 or 9 wherein the polyhydric alcohol comprises at least one alcohol selected from the group consisting of ethylene glycol, propylene glycol, isobutylene glycol, 1,3-butylene glycol, polyethylene glycol having a molecular weight of not exceeding 1500, polypropylene glycol having a molecular weight of not exceeding 500, glycerin and diglycerin.

19. A gel composition as set forth in claim 8 or 9 wherein the polyhydric alcohol comprises at least one alcohol selected from the group consisting of glycerin, diglycerin and polyethylene glycol having a molecular weight of not exceeding 1500.

20. A composition as set forth in claim 8 or 9 wherein the polyhydric alcohol is glycerin.

21. A substantially homogeneous gel composition comprising oil incorporated in a gelatinizing agent composition according to claim 3 wherein the oil is incorporated in an admixture of (b) with a solution of (a) and (c).

22. A substantially homogeneous gel composition comprising oil incorporated in a gelatinizing agent composition according to claim 3 wherein the polyhydric alcohol fatty-acid ester has an HLB value of not more than 6.

23. A gel composition as set forth in claim 22 wherein the polyhydric alcohol fatty-acid ester has an HLB value of from 4 to 6.

24. A composition according to claim 1 or 8 wherein the gelatinizing agent composition comprises from 5 to 80 percent by weight of the sucrose fatty-acid ester and substantially all of the remainder the polyhydric alcohol.

25. A composition according to claim 3 or 9 wherein the gelatinizing agent composition comprises from 1 to 50 percent by weight of the polyhydric alcohol fatty-acid ester.

26. A composition according to claim 3 or 9 wherein the total HLB value of the sucrose fatty-acid ester and the polyhydric alcohol fatty-acid ester in the gelatinizing agent composition is at least 8.

27. A composition according to claim 3 or 9 wherein the polyhydric alcohol fatty-acid ester consists mainly or entirely of at least one polyhydric alcohol fatty-acid monoester.

28. A composition according to claim 3 or 9 wherein the polyhydric alcohol fatty-acid ester is a fatty-acid ester of at least one polyhydric alcohol selected from the group consisting of glycerin, pentaerythritol, sorbitol, mannitol, diglycerin and sorbitan.

29. A composition according to claim 3 or 9 wherein the polyhydric alcohol fatty-acid ester has a fatty-acid residue with from 6 to 30 carbon atoms.

30. A composition as set forth in claim 29 wherein the polyhydric alcohol fatty-acid ester has a fatty-acid residue with from 12 to 18 carbon atoms.

31. A composition according to claim 3 or 9 wherein the polyhydric alcohol fatty-acid ester is a fatty-acid ester of sorbitan and/or of glycerin.

32. A substantially homogeneous gel composition comprising oil incorporated in a gelatinizing agent composition according to claim 2 or 4.

33. A gel composition as set forth in claim 32 which is substantially water free.

34. A gel composition as set forth in claim 8 or 9 comprising from 47 to 97 percent by weight of the oil.

35. A gel composition as set forth in claim 34 which is an oil-in-polyhydric alcohol gel.

36. A gel composition as set forth in claim 8 or 9 which comprises from 50 to 95% by weight of oil.

37. An aqueous emulsion which is an admixture of water with a gel composition according to claim 8 or 9.

38. A process for forming a homogeneous and stable gel with an oil content of from 47 to 97 percent by weight which comprises adding sufficient oil to and admixing it with a composition according to claim 1 or 3.

39. A process for forming an aqueous emulsion which comprises admixing water with a gel composition according to claim 8 or 9.

40. A gel composition as set forth in claim 8 or 9 wherein the oil is animal oil, vegetable oil, silicone oil, oil of mineral origin, water-insoluble higher alcohol, higher fatty acid, water-insoluble fatty acid alkyl ester, or a mixture thereof.

41. A gel composition as set forth in claim 40, wherein oil comprises animal oil selected from the group consisting of squalane, mink oil, turtle oil, beeswax, spermaceti, lanolin and a lanolin derivative.

42. A gel composition as set forth in claim 40 wherein oil comprises vegetable oil selected from the group consisting of cacao butter, castor oil, olive oil, corn oil, soy bean oil, tubaki oil, cotton seed oil, sesame oil, safflower oil, Japan wax and coconut oil.

43. A gel composition as set forth in claim 40, wherein the oil comprises, as oil of mineral origin, liquid paraffin, polybutene, Vaseline, paraffin wax, ceresin, microcrystalline wax or polyethylene powder.

44. A gel composition as set forth in claim 40 wherein the oil comprises, as fatty acid alkyl ester, is isopropylmyristate, isocetylmyrystate or cetylisooctanoate, candelilla wax or carnauba wax.

45. A gel composition as set forth in claim 40 wherein the oil comprises, as higher fatty acid, isostearic acid or lauric acid.

46. A gel composition as set forth in claim 40 wherein the oil comprises, as alcohol, isostearyl alcohol, oleyl alcohol, cetyl alcohol or stearyl alcohol.

47. A gelatinizing agent composition as set forth in claim 4 which comprises 9–50% by weight hydrophilic sucrose fatty acid ester, 30–90% by weight hydrophilic liquid polyhydric alcohol and 1–20% by weight lipophilic polyhydric alcohol fatty acid ester.

* * * * *

UNITED STATES PATENT AND TRADEMARK OFFICE
CERTIFICATE OF CORRECTION

PATENT NO. : 4,379,755
DATED : April 12, 1983
INVENTOR(S) : Mikio YAMADA and Yujin TABATA It is certified that error appears in the above-identified patent and that said Letters Patent are hereby corrected as shown below:

Column 1, line 68, "water-soluble" should read --water-insoluble--.
Column 2, line 49, "prefereably" should read --preferably--; line 66, "ricinolate" should read --ricinoleate--. Column 3, line 64, "homogenous" should read --homogeneous--. Column 4, line 14, "cetylisooctansate" should read --cetylisooctanoate--; line 32, "such as" should read --such is--. Column 6, line 44, "can not" should read --cannot--. Column 8, line 9, "waterwashability" should read --water washability--. Column 9, line 43, "butyl" should read --batyl--; line 61, "cleasing" should read --cleansing--. Column 10, line 8, "squalane" should read --squalene--. Claim 41, column 14, line 41, "wherein oil" should read --wherein the oil--. Claim 42, column 14, line 45, "oil comprises" should read --the oil comprises--. Claim 44, column 14, line 54, "is isopropyl-" should read --isopropyl- --.

Signed and Sealed this

Fifteenth Day of November 1983

[SEAL]

Attest:

GERALD J. MOSSINGHOFF

Attesting Officer

Commissioner of Patents and Trademarks